(12) United States Patent
Crotty et al.

(10) Patent No.: US 6,696,068 B2
(45) Date of Patent: Feb. 24, 2004

(54) COSMETIC CREAM CLEANSER

(75) Inventors: Brian Andrew Crotty, Branford, CT (US); Craig Stephen Slavtcheff, Guilford, CT (US); Michael Charles Cheney, Fairfield, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 3 days.

(21) Appl. No.: 09/854,372

(22) Filed: May 11, 2001

(65) Prior Publication Data

US 2003/0068342 A1 Apr. 10, 2003

(51) Int. Cl.$^7$ .............................. A61K 7/00; A61K 7/06; A61K 7/075; A01N 25/00; C11D 3/08
(52) U.S. Cl. ................. 424/401; 424/70.22; 424/70.11; 424/70.24; 424/486; 514/844; 510/130
(58) Field of Search ............................ 424/401, 70.22, 424/70.11, 70.24, 486; 514/844; 510/130

(56) References Cited

U.S. PATENT DOCUMENTS

| 5,236,710 A | 8/1993 | Guerrero et al. |
| 5,302,378 A | 4/1994 | Crotty et al. |
| 5,336,497 A | 8/1994 | Guerrero et al. |
| 6,113,892 A | 9/2000 | Newell et al. |
| 6,264,964 B1 * | 7/2001 | Mohammadi ............... 424/401 |

FOREIGN PATENT DOCUMENTS

| WO | 95/20376 | 8/1995 |
| WO | 98/01110 | 1/1998 |

* cited by examiner

*Primary Examiner*—Sreeni Padmanabhan
*Assistant Examiner*—Gina C. Yu
(74) *Attorney, Agent, or Firm*—Milton L. Honig

(57) ABSTRACT

A cosmetic cream cleansing composition is provided based on the presence of a silicate, a crosslinked carboxyvinyl polymer, a silicone copolyol sulfosuccinate and a carrier. The composition has a viscosity from about 20,000 to about 500,000 centipoise. The combination of components achieves a product of good viscosity, pleasant skinfeel, rich lather and phase stability.

6 Claims, No Drawings

COSMETIC CREAM CLEANSER

BACKGROUND OF THE INVENTION

1. Field of the Invention

The invention concerns a cosmetic cream for cleansing skin and having excellent skinfeel properties.

2. The Related Art

Cream type cosmetic cleansers are difficult to formulate. The term "cream" requires both opacity and a certain thickness. Consumers associate the attributes of opacity and thickness with creamy products. Chemicals imparting these properties can interfere with lathering, phase stability on storage and skinfeel.

U.S. Pat. No. 5,336,497 (Guerrero et al.) discloses cosmetic compositions functioning to remove soil from body surfaces. A combination of silicone copolyol sulfosuccinate and an amphoteric surfactant are employed to achieve a cleaning result.

U.S. Pat. No. 5,236,710 (Guerrero et al.) is a related disclosure reporting on a combination of an anionic sulfosuccinate and an emulsifying polyacrylate. More particularly the patent refers to a silicone copolyol sulfosuccinate and an acrylate/$C_{10}$–$C_{30}$ alkyl acrylate crosspolymer.

U.S. Pat. No. 6,113,892 (Newell et al.) discloses compositions delivering both a cleansing action and conditioning. Products disclosed include components which must be selected from a high foaming anionic surfactant, a polymeric cationic conditioning agent, a silicone copolyol sulfosuccinate, an emollient and water.

Although there have been some significant advances in this art, improvements are still necessary to achieve creamy products with thickness and the proper aesthetics.

Accordingly, it is an object of the present invention to provide a cosmetic cream cleanser which delivers a dense luxurious foam.

Another object of the present invention is to provide a cosmetic cream cleanser which is opaque and thick with nevertheless good lather characteristics.

These and other objects of the present will become more readily apparent from consideration of the summary and detailed description which follows.

SUMMARY OF THE INVENTION

A cosmetic cream cleanser composition is provided which includes:

(i) from about 0.1 to about 20% of a silicate;
(ii) from about 0.001 to about 2% of a crosslinked carboxyvinyl polymer other than a long chain $C_{10}$–$C_{30}$ alkyl acrylate or methacrylate containing polymer;
(iii) from about 0.01 to about 40% of a silicone copolyol sulfosuccinate; and
(iv) a cosmetically acceptable carrier;

wherein the composition has a viscosity ranging from about 20,000 to about 500,000 cp.

DETAILED DESCRIPTION OF THE INVENTION

Now it has been discovered that a combination of a silicate, a crosslinked carboxyvinyl polymer and a silicone copolyol sulfosuccinate results in a cream cleansing composition with highly desirable characteristics. These include excellent lather, good storage stability and a rich skinfeel.

A first element of the present invention is that of a silicate. Illustrative of this category are aluminum magnesium silicate, magnesium silicate, aluminum silicate, chemically modified magnesium aluminum silicate, smectite clay, bentonites, hectorites, pyrogenic colloidal silica, organically modified montmorillonite clay, hydrated aluminum silicate, fumed silica, barium silicate, calcium silicate, alumina, zeolite and combinations thereof. Particularly preferred is aluminum magnesium silicate available commercially under the trademarks of Gel White and Veegum.

Advantageously, the silicates will be finally divided powders having an average particle size ranging from about 0.0001 micron to about 50 micron, preferably from about 0.01 micron to about 10 micron, more preferably from about 0.1 to about 1.5 micron. Amounts of the silicate may range from about 0.1 to about 20%, preferably from about 0.5 to about 10%, optimally from about 1 to about 5% by weight of the composition.

A second element of the present invention is that of a crosslinked carboxyvinyl polymer other than a long chain $C_{10}$–$C_{30}$ alkyl acrylate or methacrylate containing polymer. Illustrative are acrylic acid/ethyl acrylate copolymers and the carboxyvinyl polymers sold under the Carbopol® trademark. The latter consists essentially of a colloidally water-soluble polyalkenyl polyether crosslinked polymer of acrylic acid crosslinked with from 0.75% to 2.00% of a crosslinking agent such as a polyallyl sucrose or polyallyl pentaerythritol. Specific commercial examples include Carbopol® 934, Carbopol® 940, Carbopol® 950, Carbopol® 951, Carbopol® 980, Carbopol® 981 and Carbopol® 1342. Particularly useful in Carbopol® 934, a water-soluble polymer of acrylic acid crosslinked with about 1% of a polyallyl ether of sucrose having an average of about 5.8 allyl groups for each sucrose molecule. These materials are described in U.S. Pat. No. 2,798,053 (Brown) herein incorporated by reference. Long chain fatty group substituted polymeric ester of acrylic or methacrylic acid such as Pemulen® with CTFA name of acrylates/C10–30 alkyl acrylate crosspolymer are outside the scope of this invention. Amounts of the polymer may range from about 0.001 to about 2%, preferably from about 0.005 to about 1%, optimally from about 0.01 to about 0.1% by weight of the composition.

Another important element of the present invention is that of a silicone copolyol sulfosuccinate.

The preferred silicone copolyol sulfosuccinate is of the formula:

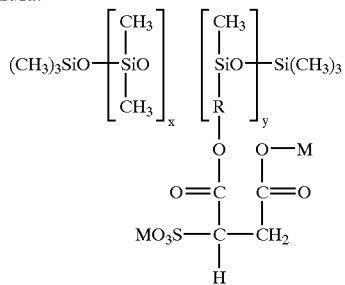

wherein R is an alkylene oxide polymer; M is a cation selected from the group consisting of hydrogen, alkali metal, alkaline earth metal, ammonium and alkanolammonium ions, x and y range in value so as to produce a compound with an equivalent weight between 700 and 1600 grams. R may be further defined as a polymer of ethylene or propylene oxide in the following forms:

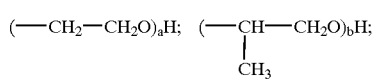

wherein a and b range in value from 1 to 30; and

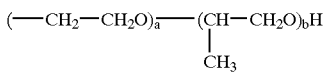

wherein a and b may range in value from 0 to 30.

A related preferred silicone copolyol sulfosuccinate structure according to the present invention is represented by the formula:

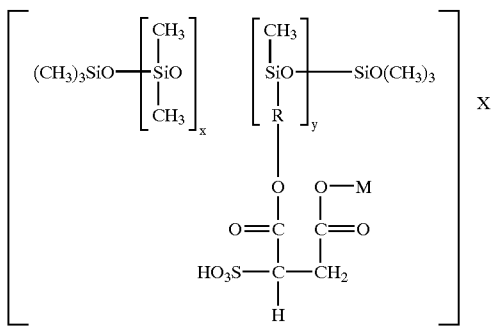

wherein X is an amine group obtained from alcohol amines, ethoxylates or propoxylates, preferably derived from the group consisting of monoethanolamine, diethanolamine, triethanolamine, monoisopropanolamine or diglycolamine.

A further related preferred silicone copolyol sulfosuccinate structure according to the present invention is represented by the formula:

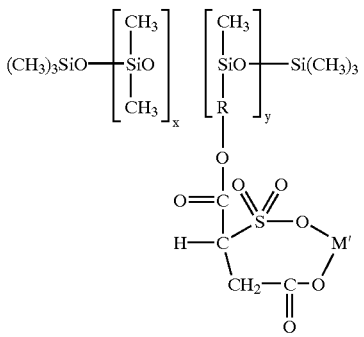

wherein M' is an alkaline earth metal, for example, calcium, magnesium or barium, rather than an alkali metal.

A still further related preferred silicone copolyol sulfosuccinate structure according to the present invention is represented by the following formula:

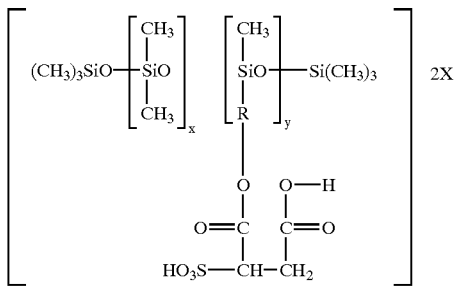

wherein X is an amine group as described above and obtained from sulfite salts containing the amine group.

The silicone copolyol sulfosuccinates of the present invention are generally prepared by reacting the ethoxylated polyether side chains of dimethicone copolyol with maleic anhydride to form a monoester and then converting the monoester to sulfosuccinate by sulfonation of the double bond with a metallic sulfite. Metallic sulfite and amine salts may also be used either alone or in combination for sulfonation of the double bond. The resulting sulfosuccinate is a silicone-based surfactant which exhibits highly improved mildness and foam stabilizing properties.

Commercially, the silicone copolyol sulfosuccinates are available from the McIntyre Chemical Company under the trademark of Mackanate DC-30 and DC-30A.

Amounts of the silicone copolyol sulfosuccinate for use in compositions of the present invention may range from about 0.01 to about 40%, preferably from about 0.1 to about 20%, more preferably from about 0.2 to about 10%, optimally between about 0.3 and about 2% by weight.

An optional further component of cosmetic cream compositions according to the present invention is that of an anionic co-surfactant. Illustrative but not limiting examples include the following classes:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono-and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3-M+)CO_2R^2$ where $R^1$ is straight or branched alkyl from about $C_8$ to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

Amounts of the anionic co-surfactant may range from about 0.1 to about 40%, preferably from about 0.5 to about 25%, optimally from about 5 to about 20% by weight of the cosmetic composition.

Surfactants other than anionics may also be present to aid in the foaming, detergency and mildness properties. Nonionic and amphoteric actives are the preferred co-surfactants. Suitable nonionic surfactants include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethyldodecylamine oxide, oleyldi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecoxy-2-hydroxypropyldi(3-hydroxypropyl)amine oxide, and dimethylhexadecylamine oxide.

Amounts of the nonionic surfactant may range from about 0.1 to about 40%, preferably from about 0.5 to about 15%, optimally from about 1 to about 5% by weight of the total composition.

Amphoteric surfactants such as betaines may also be employed as co-actives. Suitable betaines may have the general formula $RN^+(R^1)_2R^2COO^-$ wherein R is a hydrophobic moiety selected from the group consisting of alkyl groups containing from 10 to 22 carbon atoms, preferably from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each $R^1$ is an alkyl group containing from 1 to 3 carbon atoms; and $R^2$ is an alkylene group containing from 1 to about 6 carbon atoms. Sulfobetaines such as cocoamidopropyl sultaine are also suitable.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate. Most preferred is cocoamidopropyl betaine available as Tegobetaine F® sold by Th. Goldschmidt AG of Germany. Amounts of the betaine may range from about 0.05 to about 15%, preferably from about 0.5 to about 10%, optimally from about 2 to about 8% by weight of the total composition.

Moisturizing ingredients may also be included in compositions of the present invention. Water soluble moisturizers such as polyhydric alcohol-type humectants are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. For best results the humectant is preferably glycerin. The amount of humectant may range anywhere from about 0.5 to about 30%, preferably between about 1 and about 15% by weight of the composition.

Preservatives can desirably be incorporated into the cosmetic compositions of this invention to protect against the growth of potentially harmful microorganisms. Suitable traditional preservatives are EDTA salts and alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from about 0.01% to about 2% by weight of the composition.

Minor adjunct ingredients may be present in the cosmetic compositions. Among them may be the water-soluble vitamins, colorants, fragrances and botanicals. Each of these substances may range from about 0.05 to about 5%, preferably between about 0.1 and about 3% by weight.

Cationic conditioning agents in monomeric and polymeric type are also useful for purposes of this invention. Examples of the polymeric type include: cationic cellulose derivatives, cationic starches, copolymers of a diallyl quaternary ammonium salt and an acryl amide, quaternized vinylpyrrolidone, vinylimidazole polymers, polyglycol amine condensates, quaternized collagen polypeptide, polyethylene imine, cationized silicon polymer (e.g. Amodimethicone), cationic silicon polymers provided in a mixture with other components under the trademark Dow Coming 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16, etc. manufactured by the Celanese Company), quaternary ammonium salt polymers (e.g. Mirapol A-15, Mirapol AD-1, Mirapol AZ-1, etc., manufactured by the Miranol Divison of the Rhone Poulenc Company). Most preferred is polyquaternium-11 available as Luviquat® PQ 11 sold by the BASF Corporation.

Examples of monomeric cationic conditioning agents are salts of the general structure:

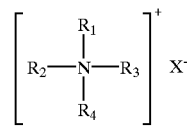

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carton atoms, or aromatic, aryl or alkaryl groups having from 12 to 22 carbon atoms; and X⁻ is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicone quats may similarly be employed. Most preferred is Silquat AD designated by the CTFA as Silicone Quaternium 8, available from Siltech Inc.

Amounts of each cationic agent may range from 0.05 to 5%, preferably from about 0.1 to about 3%, optimally from about 0.3 to about 2.5% by weight.

A cosmetically acceptable carrier is also necessary for compositions of the present invention. Most often the carrier is water. Amounts of water may range from about 2% to about 98%, preferably from about 25 to about 85%, optimally from about 40 to about 70% by weight of the composition.

Emollients may also be incorporated in compositions of the present invention. Illustrative are $C_8$–$C_{24}$ fatty acids and fatty alcohols. Representative fatty acids include lauric acid, palmitic acid, stearic acid, hydroxy stearic acid, oleic acid, behenic acid and combinations thereof. Illustrative fatty alcohols include lauryl alcohol, myristyl alcohol, cetearyl alcohol, stearyl alcohol, hydroxy stearyl alcohol, oleyl alcohol and behenyl alcohol. Amounts of the fatty acids and fatty alcohols respectively may range from about 0.1 to about 20%, preferably from about 0.5 to about 10%, optimally from about 1 to about 5% by weight of the composition.

Compositions of this invention will have a viscosity ranging from about 20,000 to about 500,000 centipoise, preferably from about 40,000 to about 100,000, optimally from about 60,000 to about 75,000 centipoise. Viscosity is measured on a Brookfield RVT Viscometer utilizing Spindle TC, rotated at 5 rpm at 22° C.

Compositions of the present invention will preferably lie within a pH range from about 3.5 to about 6.8, preferably from about 5 to about 6.

Some embodiments of the present invention may be formulated with insoluble particles to provide aesthetic appeal. These particles may be inorganic materials such as mica, titanium dioxide, fused silica or combinations. Illustrative is a mica/titanium dioxide particle sold under the Ultra Sparkle brand, available from Flamenco Inc. Particles may also be in the form of finely ground plastics such as polyolefins, polyesters and polyamides. Particularly suitable is polyethylene. Encapsulates may also serve as suspended particles. For instance, a polysaccharide such as agar, gelatin, carageenan, xanthan gum or guar gum may be dispersed as particulates. These substances can encapsulate active materials such as Vitamin C, retinol or alpha hydroxy acids. Particles for this embodiment may have an average particle size ranging from about 100 micron to about 10,000 micron, preferably from about 500 micron to about 5,000 micron, optimally from about 1,000 micron to about 3,000 micron.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate the embodiments of this invention. All parts, percentages and proportions referred to herein and in the appended claims are by weight unless otherwise indicated.

EXAMPLES 1–8

Creamy cosmetic cleanser compositions according to this invention are formulated with the components listed under Table I.

TABLE I

| INGREDIENT | EXAMPLE (Weight %) | | | | | | | |
| --- | --- | --- | --- | --- | --- | --- | --- | --- |
| | 1 | 2 | 3 | 4 | 5 | 6 | 7 | 8 |
| Water | Bal. | Bal. | Bal. | Bal. | Bal. | Bal. | Bal. | Bal. |
| Gel White ® HNF | 2.50 | — | — | 1.50 | 1.50 | 2.50 | 4.00 | — |
| Bentonite | — | 4.00 | — | — | — | — | — | 2.00 |
| Aluminum Silicate | — | — | 4.00 | — | — | — | — | — |
| Carbopol ® 980 (2% Active) | 0.06 | 0.06 | 0.12 | 0.12 | 0.12 | 0.24 | 0.24 | 0.24 |
| Disodium EDTA | 0.05 | 0.05 | 0.05 | 0.05 | 0.05 | 0.05 | 0.05 | 0.05 |
| Propylene Glycol | 8.00 | 8.00 | 8.00 | 8.00 | 8.00 | 8.00 | 8.00 | 8.00 |
| Tauranol I 87E ® (Coco-Sodium Isethionate) | 12.00 | 12.00 | 12.00 | 12.00 | 12.00 | 12.00 | 12.00 | 12.00 |
| Pristerene 4911 ® (Stearic Acid) | 4.00 | 4.00 | 4.00 | 4.00 | 4.00 | 4.00 | 4.00 | 4.00 |
| Crodacol CS-50 ® (Cetearyl Alcohol) | 2.70 | 2.70 | 2.70 | 2.70 | 2.70 | 2.70 | 2.70 | 2.70 |
| Propyparaben | 0.10 | 0.10 | 0.10 | 0.10 | 0.10 | 0.10 | 0.10 | 0.10 |
| Tegobetaine F ® (30% Active) | 8.00 | 8.00 | 8.00 | 8.00 | 8.00 | 8.00 | 8.00 | 8.00 |
| Mackanate DC-30 ® (Dimethicone Copolyol Sulfosuccinate) (30% Active) | 2.00 | 2.00 | 3.00 | 3.00 | 0.50 | 0.50 | 1.00 | 1.00 |
| Triethanolamine 99% Active | 0.415 | 0.415 | 0.83 | 0.83 | 0.83 | 1.66 | 1.66 | 1.66 |

EXAMPLE 9

A series of experiments were conducted to evaluate the physical property effects of silicate, crosslinked carboxyvinyl polymer and dimethicone copolyol sulfosuccinate. Six formulations were prepared (A–G). These are listed in the Table below.

TABLE II

| | SAMPLE WEIGHT % | | | | | | |
|---|---|---|---|---|---|---|---|
| | A | B | C | D | E | F | G |
| INGREDIENT | | | | | | | |
| Water | 61.17 | 62.17 | 61.23 | 63.73 | 63.67 | 63.67 | 61.17 |
| Gel White ® HNF | 2.50 | 2.50 | 2.50 | — | — | — | 2.50 |
| Carbopol ® 980 (2% Active) | 0.06 | 0.06 | — | — | 0.06 | — | — |
| Pemulen ® TR-Z (Acrylates/$C_{10}$–$C_{30}$ Alkyl Acrylate Crosspolymer) | — | — | — | — | — | 0.06 | 0.06 |
| Disodium EDTA | 0.05 | 0.05 | 0.05 | 0.05 | 0.05 | 0.05 | 0.05 |
| Propylene Glycol | 8.00 | 8.00 | 8.00 | 8.00 | 8.00 | 8.00 | 8.00 |
| Tauranol I 87E ® (Coco-Sodium Isethionate) | 12.00 | 12.00 | 12.00 | 12.00 | 12.00 | 12.00 | 12.00 |
| Pristerene 4911 ® (Stearic Acid) | 4.00 | 4.00 | 4.00 | 4.00 | 4.00 | 4.00 | 4.00 |
| Crodacol CS-50 ® (Cetearyl Alcohol) | 2.70 | 2.70 | 2.70 | 2.70 | 2.70 | 2.70 | 2.70 |
| Propylparaben | 0.10 | 0.10 | 0.10 | 0.10 | 0.10 | 0.10 | 0.10 |
| Tegobetaine F ® (30% Active) | 8.00 | 8.00 | 8.00 | 8.00 | 8.00 | 8.00 | 8.00 |
| Mackanate DC-30 ® (Dimethicone Copolyol Sulfosuccinate) (30% Active) | 1.00 | — | 1.00 | 1.00 | 1.00 | 1.00 | 1.00 |
| Triethanolamine (99% Active) | 0.415 | 0.415 | 0.415 | 0.415 | 0.415 | 0.415 | 0.415 |
| PROPERTIES | | | | | | | |
| Viscosity (cp)* | 68000 | 62000 | 39000 | 28000 | 32000 | 46200 | 42200 |
| Ph | 5.89 | 5.91 | 5.89 | 5.74 | 5.72 | 5.81 | 6.00 |
| OBSERVATIONS | | | | | | | |
| | Good viscosity Nice feel Good lather Phase stable at least 3 months | Good viscosity Gritty feel Good lather Phase stable | Good Viscosity Nice feel Good lather Unstable, separated in 2 weeks | Viscosity Borderline Nice feel Good lather Unstable, separated in 3 days | Good Viscosity Nice feel Good lather Unstable, separated in 3 days | Good Viscosity Nice feel Good later Unstable, separated in 4 weeks | Good Viscosity Nice feel Good lather Unstable, separation begins by 4 weeks |

*Brookfield RVT, Spindle TC, 5 cpm, 22° C.

Sample A is reflective of the present invention. This formula had a satisfactory viscosity with nice skinfeel, good lather and good storage stability. Sample B included Gel White® (silicate) and Carbopol® 980 (crosslinked carboxyvinyl polymer) but omitted the dimethicone copolyol sulfosuccinate. Although Sample B exhibited the desired high viscosity, the feel was rather gritty in a manner unacceptable to most consumers. Sample C combined the Gel White® with the dimethicone copolyol sulfosuccinate but removed Carbopol® 980. The result was a product of borderline viscosity, although having nice skinfeel and good lather. Sample C was not stable and separated within two weeks of oven storage at 50° C. Sample D omitted both Gel White® and Carbopol® 980. The result was an extremely low viscosity product that was not stable separating within three days. Sample E lacked Gel White® but did include Carbopol® 980 and dimethicone copolyol sulfosuccinate. Viscosity was found to be too low and the formula unstable separating within three days of storage at 50° C. Sample F omitted both Gel White® and Carbopol® 980. Long term stability was inadequate; separation occurred within 4 weeks at 50° C. Sample G is identical to Sample A except that Pemulen® replaces Carbopol®. Long term stability of Sample G was inadequate. Evident from this study is that all three components are necessary for the present invention.

The foregoing description and examples illustrate selected embodiments of the present invention. In light thereof variations and modifications will be suggested to one skilled in the art, all of which are within the spirit and purview of this invention.

What is claimed is:

1. A cosmetic cream cleanser composition comprising:
   (i) from about 0.1 to about 20% by weight of a silicate;
   (ii) fromF about 0.001 to about 2% by weight of a crosslinked carboxyvinyl polymer other than a long chain $C_{10}$–$C_{30}$ alkyl acrylate or methacrylate containing polymer;
   (iii) from about 0.01 to about 40% by weight of a silicone copolyol sulfosuccinate; and
   (iv) a cosmetically acceptable carrier;
   wherein the composition has a viscosity ranging from about 20,000 to about 500,000 cp.

2. The composition according to claim 1 wherein the silicate is an aluminum magnesium silicate.

3. The composition according to claim 1 wherein the silicone copolyol sulfosuccinate is a dimethicone copolyol sulfosuccinate.

4. The composition according to claim 1 wherein the silicate is present in an amount from about 1 to about 5% by weight of the composition.

5. The cosmetic composition according to claim 1 wherein the composition has a viscosity ranging from about 60,000 to about 75,000 cp.

6. A cosmetic opaque cleanser composition comprising:
   (i) from about 0.1 to about 20% by weight of an aluminum magnesium silicate;
   (ii) from about 0.001 to about 2% by weight of a crosslinked carboxyvinyl polymer other than a long chain $C_{10}$–$C_{30}$ alkyl acrylate or methacrylate containing polymer;
   (iii) from about 0.01 to about 40% by weight of dimethicone copolyol sulfosuccinate;
   (iv) a pharmaceutically acceptable carrier,
   wherein the composition has a viscosity ranging from about 20,000 to about 500,000 cp.

* * * * *